US007535570B2

(12) United States Patent
Muraishi

(10) Patent No.: US 7,535,570 B2
(45) Date of Patent: May 19, 2009

(54) ONE DIMENSIONAL MEASURING UNIT HAVING A DIELECTRIC BLOCK

(75) Inventor: Katsuaki Muraishi, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 45 days.

(21) Appl. No.: 11/245,035

(22) Filed: Oct. 7, 2005

(65) Prior Publication Data

US 2006/0082779 A1 Apr. 20, 2006

(30) Foreign Application Priority Data

Oct. 8, 2004 (JP) ............................ 2004-296435

(51) Int. Cl.
*G01N 21/55* (2006.01)

(52) U.S. Cl. ...................................................... 356/445

(58) Field of Classification Search ................. 356/246, 356/445; 436/518

See application file for complete search history.

(56) References Cited

U.S. PATENT DOCUMENTS

| | | | | |
|---|---|---|---|---|
| 5,051,586 | A * | 9/1991 | Sabreen | 250/324 |
| 5,313,264 | A * | 5/1994 | Ivarsson et al. | 356/73 |
| 5,485,277 | A * | 1/1996 | Foster | 356/445 |
| 6,738,141 | B1 * | 5/2004 | Thirstrup | 356/445 |
| 7,030,988 | B2 * | 4/2006 | Kubo et al. | 356/445 |
| 2002/0045385 | A1 * | 4/2002 | Wang | 439/610 |
| 2002/0085203 | A1 * | 7/2002 | Naya | 356/445 |
| 2002/0145737 | A1 * | 10/2002 | Kubo et al. | 356/445 |
| 2004/0090631 | A1 * | 5/2004 | Elkind et al. | 356/445 |
| 2004/0205058 | A1 | 10/2004 | Kiji | |
| 2005/0017191 | A1 * | 1/2005 | Montagu et al. | 250/393 |
| 2005/0046854 | A1 * | 3/2005 | Kunuki et al. | 356/445 |
| 2005/0220675 | A1 * | 10/2005 | Reed et al. | 422/100 |
| 2006/0017931 | A1 * | 1/2006 | Kimura | 356/445 |
| 2006/0044563 | A1 * | 3/2006 | Fujikura | 356/445 |

FOREIGN PATENT DOCUMENTS

| | | |
|---|---|---|
| JP | 6-167443 A | 6/1994 |
| JP | 2000-65731 A | 3/2000 |

OTHER PUBLICATIONS

Takayuki Okamoto, "Surface Refracto-Sensor using Evanescent Waves: Principles and Instrumentations", Spectrum Researchers, vol. 47, No. 1 (1998), pp. 19-28, Dec. 8, 1998.

* cited by examiner

*Primary Examiner*—Roy Punnoose
*Assistant Examiner*—Tara S Pajoohi
(74) *Attorney, Agent, or Firm*—Sughrue Mion, PLLC

(57) ABSTRACT

Accurate positioning of a one dimensional measuring unit in a measuring apparatus that utilizes evanescent waves is enabled. The one dimensional measuring unit is constituted by: a transparent elongate dielectric block; a thin film layer, formed on a flat surface of the dielectric block; and a flow path forming member, which is in close contact with the thin film layer of the dielectric block, for forming a plurality of flow paths in the longitudinal direction of the dielectric block on the thin film layer, with intervals therebetween. A linear guide groove for conveyance is formed in the bottom surface of the dielectric block in the longitudinal direction thereof, and positioning abutment surfaces are formed on the side surfaces and a first end surface of the dielectric block, to accurately position the measuring unit in the X, Y, and Z directions.

9 Claims, 14 Drawing Sheets

20
19
18
17
17
16
16
VII
VII
10
54a
52b
54a
54
52
62
63
64
15b
15b
15c
15d
15a
13
14

70
72
71
60
54a
54a
54
53
52
51
62
64
55
50
50f
63
50g
73

SIGNAL PROCESSING SECTION
DRIVER
DISPLAY
20
19
21
18
17
17a
17b
17c...
16
D
10
12
51
55
50
11b
50d
11
11a
50e
50f,50g
Z
X
62,64
63
15
15b
15c
15a
13
14

B
111
10
10
100a
A
100
100

11
10
10
100
100
100a
100a 140
145
144
142
143
141
100
100

ONE DIMENSIONAL MEASURING UNIT HAVING A DIELECTRIC BLOCK

BACKGROUND OF THE INVENTION

1. Field of the Invention

The present invention relates to a measuring unit, to be employed in a measuring apparatus that causes a light beam to be totally internally reflected at an interface between a thin film layer, which is in contact with a measurement target such as a sample, and a dielectric block, to generate evanescent waves, and that measures changes in the intensity of the totally internally reflected light beam due to the evanescent waves, to analyze the sample. Particularly, the present invention relates to a one dimensional measuring unit, which is equipped with a plurality of measurement stations arranged in the longitudinal direction thereof.

2. Description of the Related Art

Surface plasmon sensors are known, as a type of measuring apparatus that utilizes evanescent waves. In metals, free electrons oscillate in groups to generate compression waves, called plasma waves. The compression waves which are generated at the surface of metals are called surface plasmon, when quantized. Various known surface plasmon sensors utilize a phenomenon, in which the surface plasmons are excited by light waves, to analyze properties of samples. Particularly well known surface plasmon sensors are those of a Kretschmann configuration (as disclosed in Japanese Unexamined Patent Publication No. 6(1994)-167443, for example).

Surface plasmon sensors of the Kretschmann configuration basically comprise: a dielectric block, shaped as a prism, for example; a metal film, formed on one surface of the dielectric block and which is brought into contact with a sample; a light source for emitting a light beam; an optical system for causing the light beam to enter the dielectric block at various angles of incidence so that total internal reflection conditions are satisfied at an interface of the dielectric block and the metal film; a photodetecting means for detecting the intensity of the light beam, which has been totally reflected at the interface; and a measuring means for measuring the state of surface plasmon resonance, based on detection results obtained by the photodetecting means.

In order to obtain various angles of incidence for the light beam, a comparatively thin incident light beam may be caused to impinge upon the interface while changing the angle of incidence. Alternatively, a comparatively thick incident light beam may be caused to impinge upon the interface in the form of convergent light or divergent light, so that the incident light beam includes components impinging upon the interface at various angles. In the former case, the light beam which is reflected from the interface at an angle, which varies as the angle of incidence changes, may be detected by a small photodetector which is moved in synchronization with the change of the angle of incidence, or by an area sensor that extends in the direction coincident with the angles of reflected light. In the latter case, an area sensor, which extends in directions such that all the components of light reflected from the interface at various angles can be detected thereby, may be employed.

In a surface plasmon sensor of the construction described above, when a light beam impinges upon the metal film at a particular angle of incidence $\theta_{sp}$ greater than or equal to the angle of total internal reflection, evanescent waves having an electric field distribution in a sample which is in contact with the metal film are generated, and surface plasmon is excited at an interface between the metal film and the sample. When the wave vector of the evanescent light is equal to the wave number of the surface plasmon and wave number matching is established, the evanescent waves and the surface plasmon resonate and light energy is transferred to the surface plasmon, whereby the intensity of light reflected in total internal reflection at the interface of the dielectric block and the metal film sharply drops. The sharp intensity drop is generally detected as a dark line by the photodetector.

When the wave number of the surface plasmon can be known from the angle of incidence $\theta_{sp}$ at which the phenomenon of attenuation in total internal reflection (ATR) takes place, the dielectric constant of the sample can be obtained. That is, $$K_{sp}(\omega) = \frac{\omega}{c}\sqrt{\frac{\varepsilon_m(\omega)\varepsilon_s}{\varepsilon_m(\omega)+\varepsilon_s}}$$

wherein $K_{sp}$ represents the wave number of the surface plasmon, ω represents the angular frequency of the surface plasmon, c represents the speed of light in a vacuum, and $\in$m and $\in$s respectively represent the dielectric constants of the metal and the sample.

When the dielectric constant $\in$s of the sample is known, the refractive index and the like of the sample can be determined on the basis of a predetermined calibration curve or the like. As a result, properties of the sample related to the refractive index, such as the dielectric constant, can be determined, by determining the angle $\theta_{sp}$ at which attenuated total reflection occurs (hereinafter, referred to as "attenuated total reflection angle $\theta_{sp}$").

As a similar type of sensor that utilizes evanescent waves, there is known a leaky mode sensor as described in, for instance, "Surface Refracto-Sensor using Evanescent Waves: Principles and Instrumentations" by Takayuki Okamoto, Spectrum Researches, Vol. 47, No. 1 (1998), pp. 19-28. The leaky mode sensor basically comprises: a dielectric block, shaped as a prism, for example; a cladding layer, formed on one surface of the dielectric block; an optical waveguide layer, which is formed on the cladding layer and which is brought into contact with a sample; a light source for emitting a light beam; an optical system for causing the light beam to enter the dielectric block at various angles of incidence so that total internal reflection conditions are satisfied at an interface of the dielectric block and the cladding layer; a photodetecting means for detecting the intensity of the light beam, which has been totally reflected at the interface; and a measuring means for measuring the state of excitation of a waveguide mode, based on detection results obtained by the photodetecting means.

In a leaky mode sensor of the construction described above, when the light beam is caused to impinge upon the cladding layer through the dielectric block at an angle greater than or equal to an angle of total internal reflection, evanescent waves are generated in the optical waveguide layer and an evanescent wave having a particular wave number comes to propagate through the optical waveguide layer in a waveguide mode. When the waveguide mode is thus excited, almost all the incident light which generates the evanescent wave having a particular wave number is taken into the optical waveguide layer and accordingly, the intensity of light reflected in total internal reflection at the interface of the dielectric block and the clad layer sharply drops. Because the wave number of light to be propagated through the optical waveguide layer depends upon the refractive index of the sample on the optical waveguide layer, the refractive index and properties of the sample related to the refractive index can be determined, based on the attenuated total reflection angle $\theta_{sp}$.

The aforementioned surface plasmon sensors and leaky mode sensors may be utilized to perform random screening in the field of pharmaceutical manufacture. In random screening, specific substances that bond with a desired sensing substance are sought. In this case, the sensing substance is disposed on the thin film (the metal film in the case of a surface plasmon sensor, and the optical waveguide layer and the cladding layer in the case of a leaky mode sensor). Then, various solutions of test targets (sample liquids) are added to the sensing substance. Each time that a predetermined amount of time passes, the attenuated total internal reflection angle $\theta_{sp}$ is measured. If the test target binds with the sensing substance, the refractive index of the sensing substance changes over time due to the bond. Accordingly, whether the test target is bonding with the sensing substance, that is, whether the test target is the specific substance that bonds with the sensing substance, can be determined by measuring the attenuated total internal reflection angle $\theta_{sp}$ at predetermined time intervals, thereby measuring whether the attenuated total reflection angle $\theta_{sp}$ changes. A combination of an antigen and an antibody is an example of the combination of the specific substance and the sensing substance. Alternatively, a combination of an antibody and another antibody may be the combination of the specific substance and the sensing substance. Measurement regarding whether a rabbit antihuman IgG antibody, as a sensing substance, bonds with an antihuman IgG antibody, as a specific substance, and quantitative analysis of the bond, are specific examples of measurement.

Note that it is not necessary to detect the attenuated total reflection angle $\theta_{sp}$ itself, in order to measure bonding states between test targets and sensing substances. For example, a sample liquid may be added to a sensing substance, then the variation in the attenuated total reflection angle $\theta_{sp}$ may be measured. The bonding state may be measured, based on the degree of the variation of the attenuated total reflection angle $\theta_{sp}$.

Meanwhile, there are known sensors that perform measurements by employing a planar measuring chip, on which a sensing substance is fixed. Liquid samples are continuously supplied to the measuring chip via a flow path mechanism (as disclosed in, for example, Japanese Unexamined Patent Publication No. 2000-065731). In this type of sensor, when measuring a bonding state between the sensing substance and a specific substance, fresh liquid samples are constantly supplied to the measuring chip. Therefore, the concentration of the test target within the sample liquid remains constant, and measurement of the bonding state can be performed favorably. In addition, if bonding continues to occur after measurement of the bonding state between the sensing substance and the specific substance, a liquid sample that does not include the specific sample may be caused to flow over the measuring chip, on which the bonded compound is fixed. Thereby, a dissociating state of the sensing substance and the specific substance can be measured. Further, in cases that a gas, or a liquid sample in which gas is included, is employed as a sample, the sample can be easily supplied to the measuring chip, by use of the flow path mechanism.

In recent years, various types of solvent mediums are being employed, accompanying the diversity of reactions to be detected. Among the solvent mediums, there are those, such as water, which are likely to evaporate. Evaporation of water, when used as a solvent medium, changes the refractive index of the measurement sample, which changes the measurement signal. Therefore, there are cases that accurate measurement becomes difficult. In these cases, it is possible to minimize evaporation of the measurement sample and thereby stabilize the measurement signal, by providing the aforementioned flow path mechanism.

Various advantageous are obtained by providing the flow path mechanism, as described above. However, there are drawbacks, such as a long piping system being required to supply the samples onto the measuring chip, and a large amount of the sample being necessary.

Therefore, a so-called one dimensional measurement unit has been proposed in U.S. Patent Application Publication No. 20040205058. This measuring unit comprises: an elongate dielectric block, which is transparent with respect to a light beam; a thin film layer, formed on a flat surface of the dielectric block; and a flow path forming member, which is in close contact with the thin film layer of the dielectric block, for forming a plurality of flow paths in the longitudinal direction of the dielectric block on the thin film layer, with intervals therebetween. The flow paths are designated as measurement paths on the thin film layer. The ends of each flow path are in communication with an entrance and an exit of the flow path forming member, to form supply paths and discharge paths. Pipettes are provided at the entrance and the exit of the flow path forming member, to supply and discharge liquid samples.

Liquid samples are enabled to be supplied to the entrance of the flow path forming member of the one dimensional measuring unit as described above by an external liquid supplying component, such as a pipette chip. Therefore, a flow path mechanism for supplying a sample to the thin film layer is provided, while the necessity of the long piping system is obviated. Accordingly, it is possible to perform measurements with a small amount of the sample.

However, in order to accurately set the long measurement unit at a predetermined position, protrusive portions that protrude from the two ends of the measuring unit are held to handle the measuring unit. Therefore, a holding mechanism must be capable of accurate movement in the X, Y, and Z directions, which complicates the holding mechanism. In addition, positional displacement during readout becomes likely to occur, which is not favorable from a practical point of view.

SUMMARY OF THE INVENTION

The present invention has been developed in view of the above circumstances. It is an object of the present invention to provide a one dimensional measuring unit, which is capable of being accurately set in a predetermined position in the X, Y, and Z directions with a simple structure, which does not require a complex holding mechanism, and in which positional displacement during readout is not likely to occur.

The one dimensional measuring unit of the present invention comprises:

an elongate dielectric block, which is transparent with respect to a light beam;

a thin film layer, formed on a flat surface of the dielectric block; and a flow path forming member, which is in close contact with the thin film layer of the dielectric block, for forming a plurality of flow paths in the longitudinal direction of the dielectric block on the thin film layer, with intervals therebetween;

each of the plurality of flow paths being constituted by: a measurement path, formed on the thin film layer; a supply path that extends from the entrance of the flow path forming member to the measurement path; and a discharge path that extends from the measurement path to the exit of the flow path forming member;

a linear guide groove for conveyance being formed in the bottom surface of the dielectric block in the longitudinal direction thereof; and positioning abutment surfaces being formed on the side surfaces and a first end surface of the dielectric block.

It is preferable that the positioning abutment surfaces of the side surfaces and the first end surface are formed on the side surfaces in the vicinity of the bottom surface and on the first end surface in the vicinity of the bottom surface.

The thin film layer may be a metal film, so that the measuring unit of the present invention constitutes a measuring unit to be employed in a surface plasmon sensor that utilizes surface plasmon resonance to perform measurement. Alternatively, the thin film layer may be a cladding layer and an optical waveguide layer formed on the cladding layer, so that the measuring unit of the present invention constitutes a measuring unit to be employed in a leaky mode sensor that utilizes excitation of a waveguide mode in the optical waveguide layer to perform measurement.

The dielectric block may be in a plate form that does not include a prism. Alternatively, a prism, for reflecting a light beam emitted from a light source of a measuring apparatus and totally internally reflected at an interface between the dielectric block and the thin film layer toward a photodetecting means of the measuring apparatus, may be integrally formed with the dielectric block.

It is preferable that the flow path forming member is formed of an elastic material. In this case, it is preferable that slits or a septum is provided at the entrance and/or the exit thereof. Here, it is not necessary for the slits or the septum to be provided at the end of the entrance and/or exit of the flow path forming member. The slits or the septum may be provided in the vicinity of the entrance and/or the exit.

It is preferable for the measuring unit to further comprise a holding member, for engaging with the dielectric block and for holding the flow path forming member at the upper surface of the dielectric block. In this case, it is preferable that the holding member comprises a holding plate portion, to be placed in close contact with the surface of the flow path forming member, in which the entrance and exit are formed. It is preferable for insertion apertures, which are tapered such that the apertures become smaller toward the flow path forming member, are formed in the holding plate portion at positions that face the exit and the entrance of the flow path forming member.

It is preferable for the measuring unit of the present invention to further comprise an evaporation preventing member, for sealing the entrance and/or the exit to prevent evaporation of samples. In this case, the evaporation preventing member may be formed by an elastic material, having slits formed at the portions thereof that face the entrance and/or exit. The holding member and the evaporation preventing member may be integrally formed. Alternatively, the holding member and the evaporation preventing member may be adhesively attached to each other.

Note that when employing the measuring unit of the present invention to perform measurements regarding a target of measurement, such as a sample, that is, to obtain data regarding the refractive index of the target of measurement, the refractive index of the sample provided on the thin film layer may be obtained. Alternatively, a sensing substance, such as an antibody, may be fixed on the thin film layer, and data regarding a change in refractive index or whether a change in refractive index is present due to an antigen-antibody reaction may be obtained.

The data regarding the refractive index may be obtained by: causing a light beam to enter the interface between the dielectric block and the thin film layer at various angles of incidence; and detecting the light beam, which is reflected at the interface, to detect an attenuated total reflection angle or a change in the attenuated total reflection angle, thereby obtaining the refractive index or a change in the refractive index. Alternatively, the method disclosed in "Porous Gold in Surface Plasmon Resonance Measurement", D. V. Noort, K. Johansen, and C. F. Mandenius, EUROSENSORS XIII, 1999, pp. 585-588, may be employed. This method obtains refractive indices or changes in refractive indices for each of a plurality of wavelengths of light, by: causing light beams of a plurality of wavelengths to enter the interface at an angle of incidence that enables total internal reflection conditions to be obtained; and measuring the intensities of the totally internally reflected light beams for each wavelength, thereby measuring the degree of attenuated total reflection for each wavelength. As a further alternative, the method disclosed in "Surface Plasmon Resonance Interferometry for Micro-Array Biosensing", P. I. Nikitin, A. N. Grigorenko, A. A. Beloglazov, M. V. Valeiko, A. I. Savchuk, and O. A. Savchuk, EUROSENSORS XIII, 1999, pp. 235-238, may be employed. This method obtains data regarding changes in the refractive index, by: causing a light beam to enter the interface at an angle of incidence that enables obtainment of total internal reflection conditions; separating a portion of the light beam before it reaches the interface; causing the separated portion of the light beam to interfere with the light beam, which is totally internally reflected at the interface; and detecting the interference pattern of the coherent light beam formed by the interference.

That is, the data regarding the refractive index of the target of measurement may be any data that changes corresponding to the refractive index of the target of measurement. Examples of such data are: the attenuated total reflection angle, which changes according to the refractive index of a target of measurement; the wavelength of a light beam that causes total attenuated reflection; changes in the attenuated total reflection angle, which changes according to the refractive index of a target of measurement; changes in the wavelength of a light beam that causes total attenuated reflection; and changes in the interference pattern.

The one dimensional measuring unit of the present invention comprises the elongate dielectric block, in which a plurality of flow paths are formed in the longitudinal direction of the dielectric block on the thin film layer, with intervals therebetween. The dielectric block has the linear guiding groove for conveyance formed in the bottom surface thereof. Therefore, the dielectric block may be slid along a rail on the side of an apparatus, to stably guide the measuring unit in the longitudinal direction thereof. Accordingly, each of the flow paths can be guided to positions at which they face a predetermined measuring station. The dielectric block further comprises the positioning abutment surfaces at the side surfaces and at the first end surface thereof. Therefore, if positioning stoppers for abutting the abutment surfaces and means for pressing the dielectric block against the stoppers and the rail are provided on the apparatus, the dielectric block can be accurately positioned in the X, Y, and Z directions. Accordingly, accurate and stable measurements can be realized.

It is preferable that the positioning abutment surfaces of the side surfaces and the first end surface are formed on the side surfaces in the vicinity of the bottom surface and on the first end surface in the vicinity of the bottom surface. In this case, the positioning stoppers can be provided integrally with the rail, which simplifies the construction of the positioning mechanism on the apparatus.

It is preferable that the flow path forming member is formed of an elastic material. In this case, the flow path forming member can be placed in close contact with the thin film layer in a positive manner. Therefore, leakage of liquid samples from the contact surface can be prevented. Further, slits or a septum may be provided at the entrance and/or the exit of the flow path forming member. In this case, evaporation of the liquid samples can be prevented. Accordingly, changes in the refractive index of the sample, due to evaporation thereof, can be prevented, and measurement signals can be stabilized.

The measuring unit may further comprise the holding member, for engaging with the dielectric block and for holding the flow path forming member at the upper surface of the dielectric block. In this case, separation of the flow path forming member and the dielectric block during conveyance can be prevented. Therefore, the handling properties of the measuring unit are improved. The holding member may comprise the holding plate portion, to be placed in close contact with the surface of the flow path forming member, in which the entrance and exit are formed. The insertion apertures, which are tapered such that the apertures become smaller toward the flow path forming member, may be formed in the holding plate portion at positions that face the exit and the entrance of the flow path forming member. By the provision of the insertion apertures, insertion of external fluid supply components, such as pipettes and syringes, into the entrance or the exit of the flow path forming member is facilitated. The measuring unit of the present invention may further comprise the evaporation preventing member, for sealing the entrance and/or the exit to prevent evaporation of samples. In this case, evaporation of the liquid samples can be prevented. Accordingly, changes in the refractive index of the sample, due to evaporation thereof, can be prevented, and measurement signals can be stabilized. The evaporation preventing member may be formed by an elastic material, having slits formed at the portions thereof that face the entrance and/or exit. Thereby, the evaporation preventing member can be formed having a simple construction.

In the case that the holding member and the evaporation preventing member are formed integrally, the number of parts can be reduced. Accordingly, the manufacturing properties of the measuring unit can be improved.

Alternatively, in the case that the holding member and the evaporation preventing member are adhesively attached to each other, they can be formed of different materials.

The flow path forming member forms a plurality of flow paths. Therefore, it is possible to perform parallel measurement of a plurality of samples with a single measuring unit.

DESCRIPTION OF THE PREFERRED EMBODIMENTS

Hereinafter, embodiments of the present invention will be described with reference to the attached drawings.

[Measuring Unit]

Figure 1:
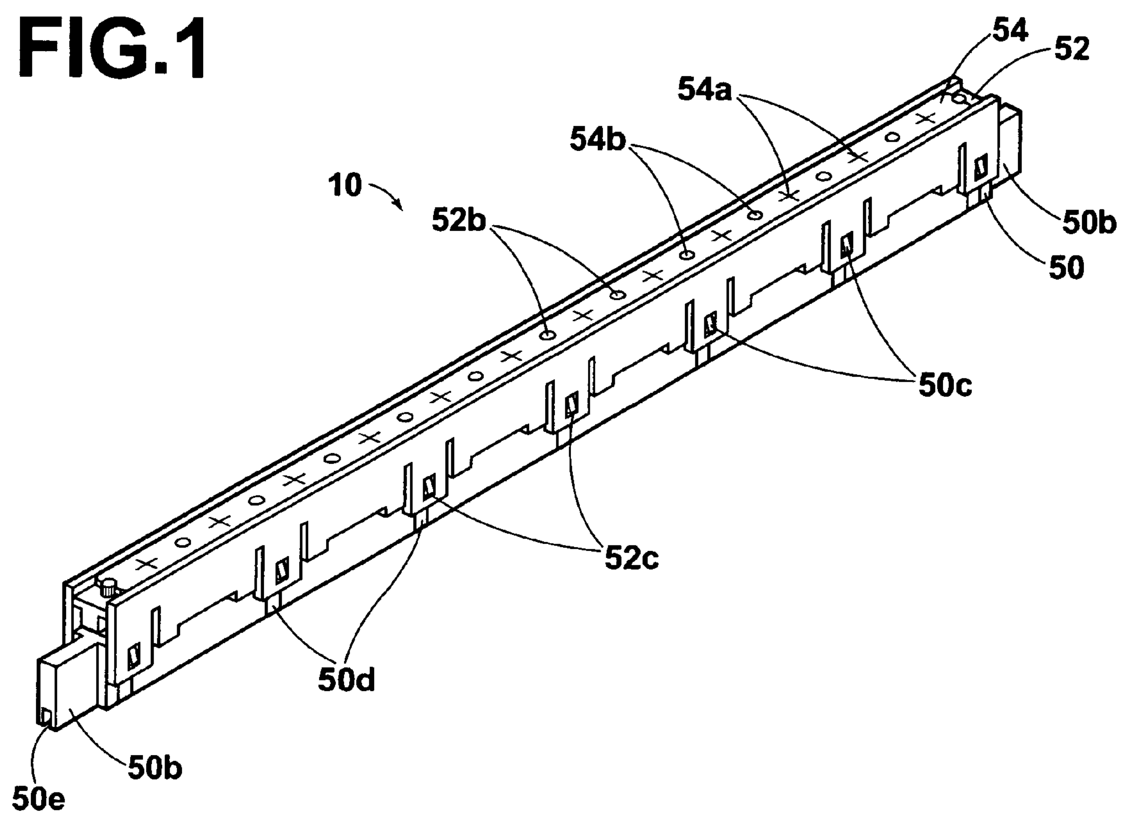
FIG. 1 is a perspective view of a measuring unit according to a first embodiment of the present invention.
Figure 2:
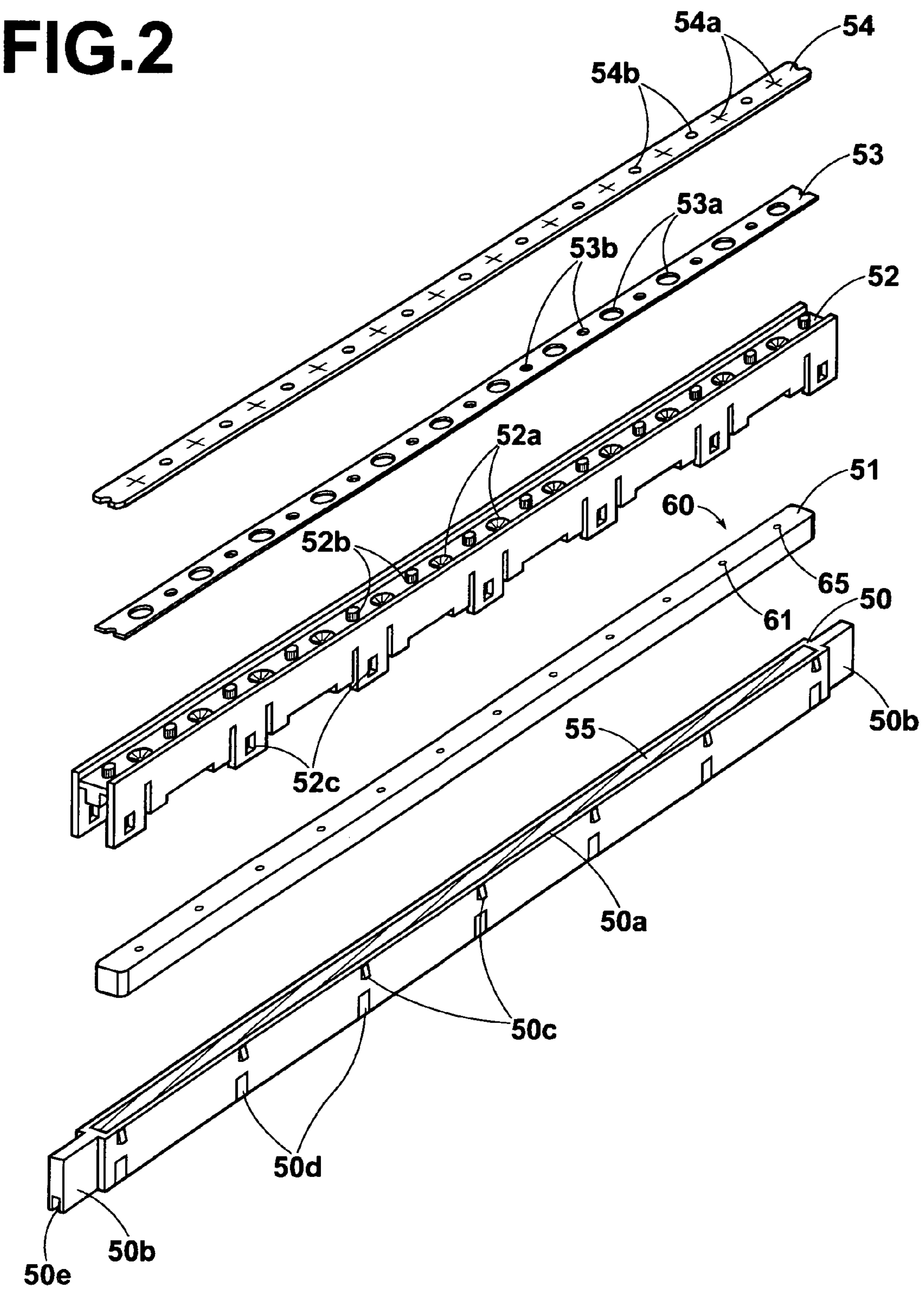
FIG. 2 is an exploded perspective view of the measuring unit of FIG. 1.
Figure 3:
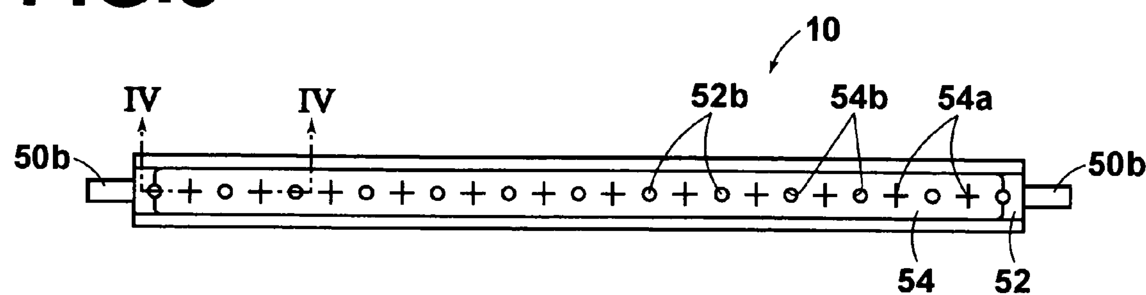
FIG. 3 is a plan view of the measuring unit of FIG. 1.
Figure 4:
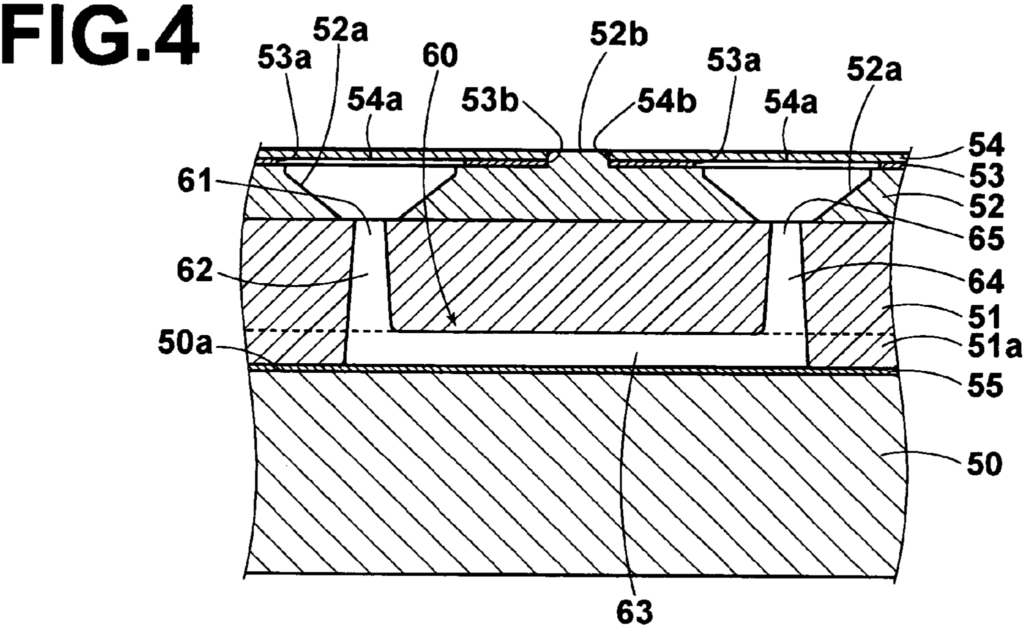
FIG. 4 is a sectional view taken along line IV-IV of FIG. 3.

FIG. 1 is a perspective view of a measuring unit 10 according to a first embodiment of the present invention. FIG. 2 is an exploded perspective view of the measuring unit 10. FIG. 3 is a plan view of the measuring unit 10. FIG. 4 is a sectional view taken along line IV-IV of FIG. 3.

The measuring unit 10 comprises: an elongate dielectric block 50, which is transparent with respect to a light beam; a metal film 55 as a thin film layer, formed on the flat upper surface 50*a* of the dielectric block; a flow path forming member 51, which is in close contact with the metal film 55 of the dielectric block 50; and a holding member 52 that engages with the dielectric block 50 and holds the flow path forming member 51 above the upper surface 50*a* of the dielectric block 50.

The dielectric block 50 is formed by a transparent resin, for example. The dielectric block 50 comprises a main body having a trapezoidal shape, in which the bottom edge is shorter than the upper edge in a cross section perpendicular to the longitudinal direction thereof; and holding portions 50*b*, which are of a thinner width than that of the main body when viewed from above (or below), are formed at each end of the main body in the longitudinal direction thereof. A prism, for causing a light beam emitted from a light source of a measuring apparatus (to be described later) to enter an interface between the dielectric block 50 and the metal film 55, and for reflecting the light beam, which is totally internally reflected at interface, toward a photodetecting means of the measuring apparatus, is integrally formed with the dielectric block 50. Engaging protrusions 50*c*, for engaging with engaging apertures 52*c* of the holding member 52, to be described later, are formed on both side surfaces of the main body. Vertically protruding protrusions 50*d* are formed on both side surfaces in the vicinity of the bottom surface such that they face each other. A guide groove 50*e* is formed in the bottom surface of the dielectric block 50. The surfaces of the vertical protrusions 50*d* are parallel with respect to each other. A positioning abutment surface 50*h* is formed at the end surface of the holding portion 50*b*, which is at the leading end of the dielectric block 50 when the dielectric block 50 is moved to a measurement station.

A plurality of flow paths 60, constituted by: a measurement path 63; a supply path 62 that extends from the entrance 61 of the flow path forming member 51 to the measurement path 63; and a discharge path 64 that extends from the measurement path 63 to the exit 65 of the flow path forming member 51; are formed along the longitudinal direction of the flow path forming member 51. The plurality of flow paths 60 are arranged linearly.

As illustrated in FIG. 4, the exit of a supply path 62 and the entrance to a discharge path 64 are open at the lower portion of the flow path forming member 51. Seals 51*a*, for surrounding the exit of the supply path 62 and the entrance of the discharge path 64, are formed at the regions of the lower surface of the flow path forming member 51 that contact the metal film 55. The interior of the seals 51*a* is the measurement path 63. That is, when the flow path forming member 51 is placed in close contact with the metal film 55 of the dielectric block 50, the measurement path 63 at the interior of the seals 51*a* functions as a flow path. The seals 51*a* may be integrally formed with the upper portion of the flow path forming member 51. Alternatively, the seals 51*a* may be formed separately from a different material, then attached to the flow path forming member 51. For example, the seals 51*a* may be O-rings or the like, which are attached to the lower portion of the flow path forming member 51.

It is presumed that a liquid sample that contains a protein will be utilized in a measuring apparatus that employs the measurement unit of the present invention, such as a surface plasmon sensor. If the protein within the liquid sample aggregates within the flow path 60, accurate measurement will become difficult. Therefore, it is preferable that the material of the flow path forming member does not have nonspecific adsorbency with respect to proteins. Specific examples of such materials are silicone and polypropylene. By forming the flow path forming member 51 with this type of elastic material, the flow path forming member 51 can be placed into positive close contact with the metal film 55. Therefore, leakage from the contact surface between the flow path forming member 51 and the metal film 55 can be prevented.

The holding member 52 is formed by an elastic material, such as polypropylene or the like. The holding member 52 has a substantially C shaped cross section in the direction perpendicular to the longitudinal direction thereof. Pipette insertion apertures 52*a*, which are tapered such that the apertures become smaller toward the flow path forming member 51, are formed in an upper plate (holding plate portion) at positions that face the entrance 61 and the exit 65 of the flow path forming member 51. Positioning bosses 52*b* are formed on the upper surface of the holding member 52 at the midpoint between each pipette insertion aperture 52*a*, and toward the exteriors of each pipette insertion aperture 52*a*.

An evaporation preventing member 54 is adhesively attached to the upper surface of the holding member 52 by means of double sided tape 53. As illustrated in FIG. 2, pipette insertion apertures 53*a* are formed in the double sided tape 53 at positions that face the pipette insertion apertures 52*a*, and positioning apertures 53*b* are formed at positions that face the bosses 52*b*. Similarly, slits 54*a* are formed in the evaporation preventing member 54 at positions that face the pipette insertion apertures 52*a*, and positioning apertures 54*b* are formed at positions that face the bosses 52*b*. The bosses 52*b* penetrate through the apertures 53*b* of the double sided tape 53 and the apertures 54*b* of the evaporation preventing member 54, and the evaporation preventing member 54 is adhesively attached to the upper surface of the holding member 52. Thereby, the slits 54*a* are aligned with the entrances 61 and the exits 65 of the flow path forming member 51. It is necessary for the evaporation preventing member 54 to be formed by an elastic material, in order to enable pipettes to be inserted through the slits 54*a*. Specific examples of such a material are silicone, polypropylene, and the like. Note that the holding member 52 and the evaporation preventing member 54 may be integrally formed. In addition, the flow path forming member 51 may also be integrally formed with the holding member 52.

The engaging apertures 52*c*, for engaging with the engaging protrusions 50*c* of the dielectric block 50, are formed in the side plates of the holding member 52. The flow path forming member 51 is sandwiched between the holding member 52 and the dielectric block 50 in a state in which the engaging apertures 52*c* and the engaging protrusions 50*c* are engaged, to mount the holding member 52 onto the dielectric block 50. By this construction, the flow path member 51 is held on the upper surface 50*a* of the dielectric block 50.

As illustrated in FIG. 4, in the state in which the flow path forming member 51 is sandwiched between the holding member 52 and the dielectric block 50, the entrances 61 and the exits 65 are sealed from the exterior by the slits 54*a* of the evaporation preventing member 54. Thereby, evaporation of liquid samples supplied to the paths 60 is prevented.

[Surface Plasmon Sensor]

Figure 5:
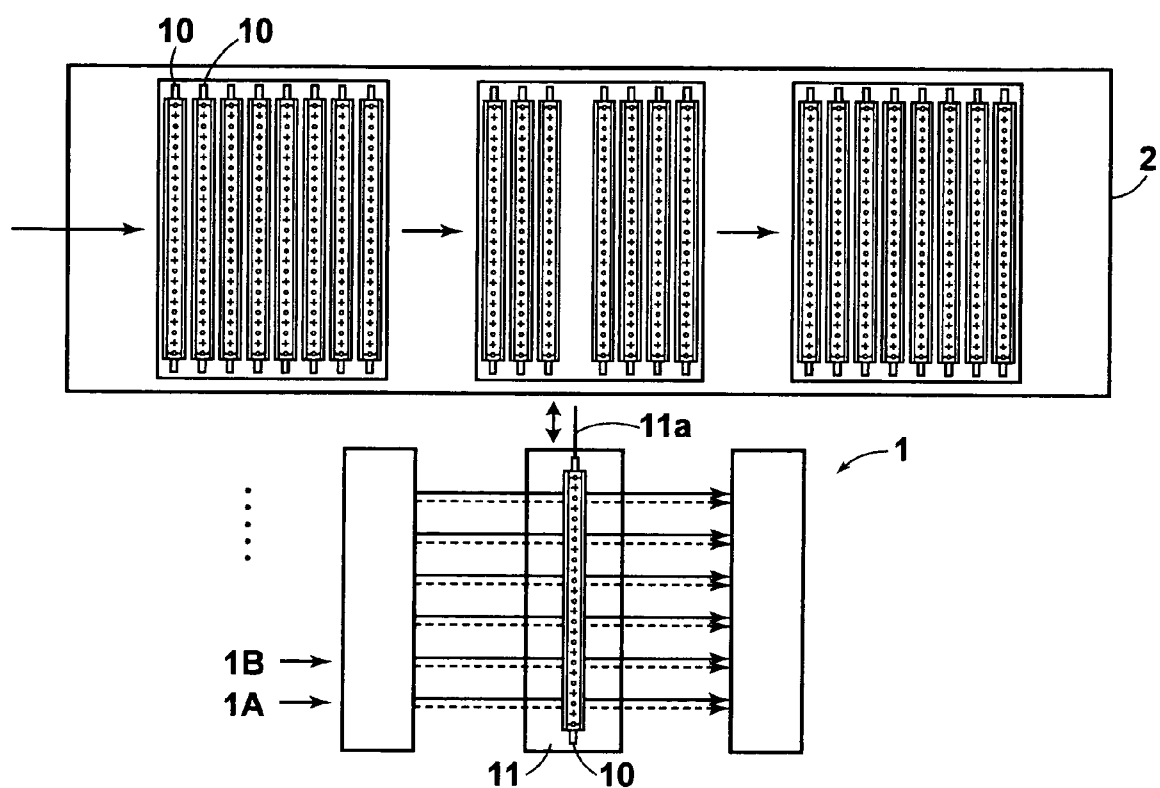
FIG. 5 is a plan view that illustrates the schematic structure of a surface plasmon sensor that employs the measuring unit of FIG. 1.
Figure 6:
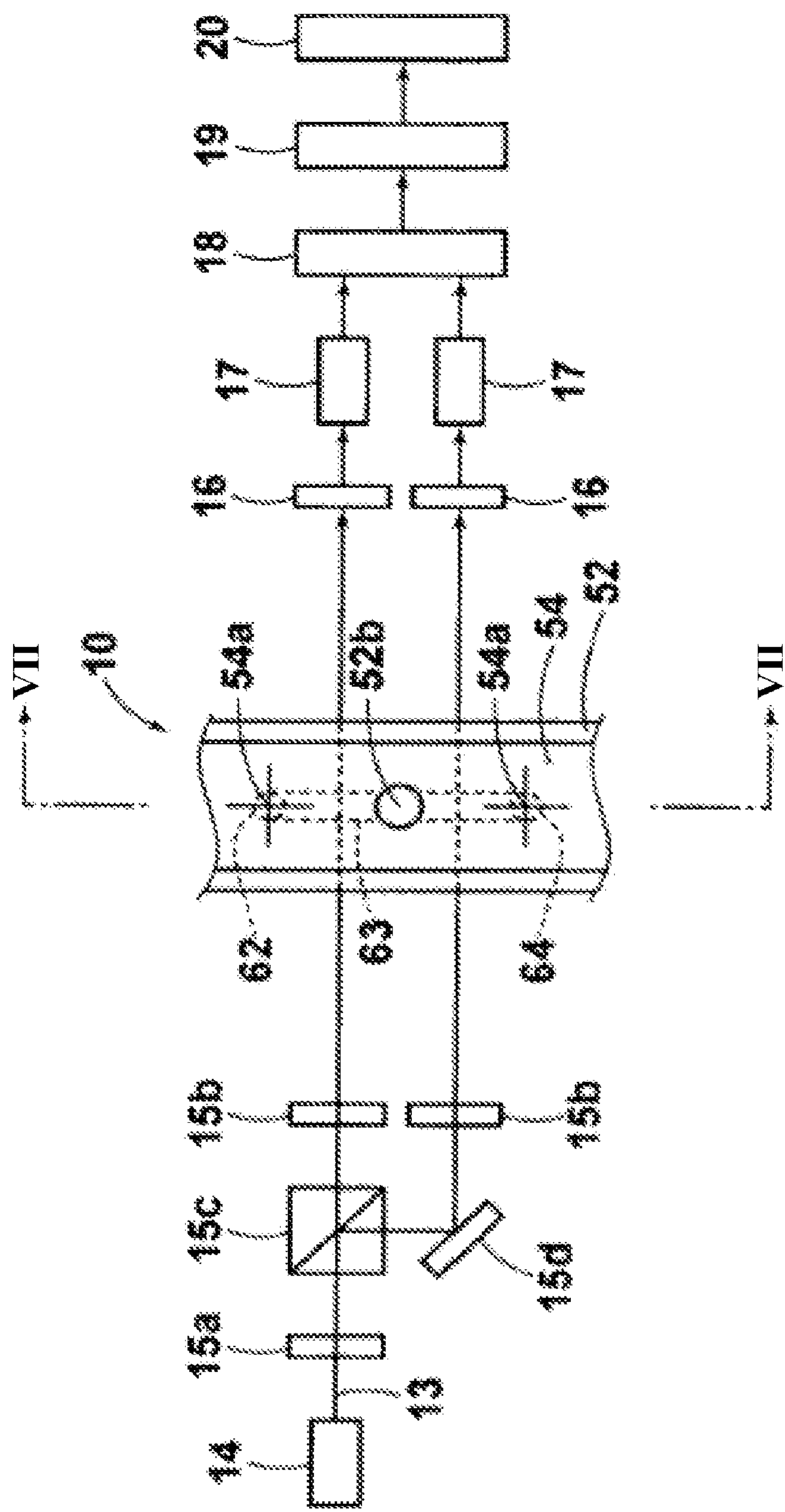
FIG. 6 is a plan view of a measuring system of the surface plasmon sensor of FIG. 5.
Figure 7:
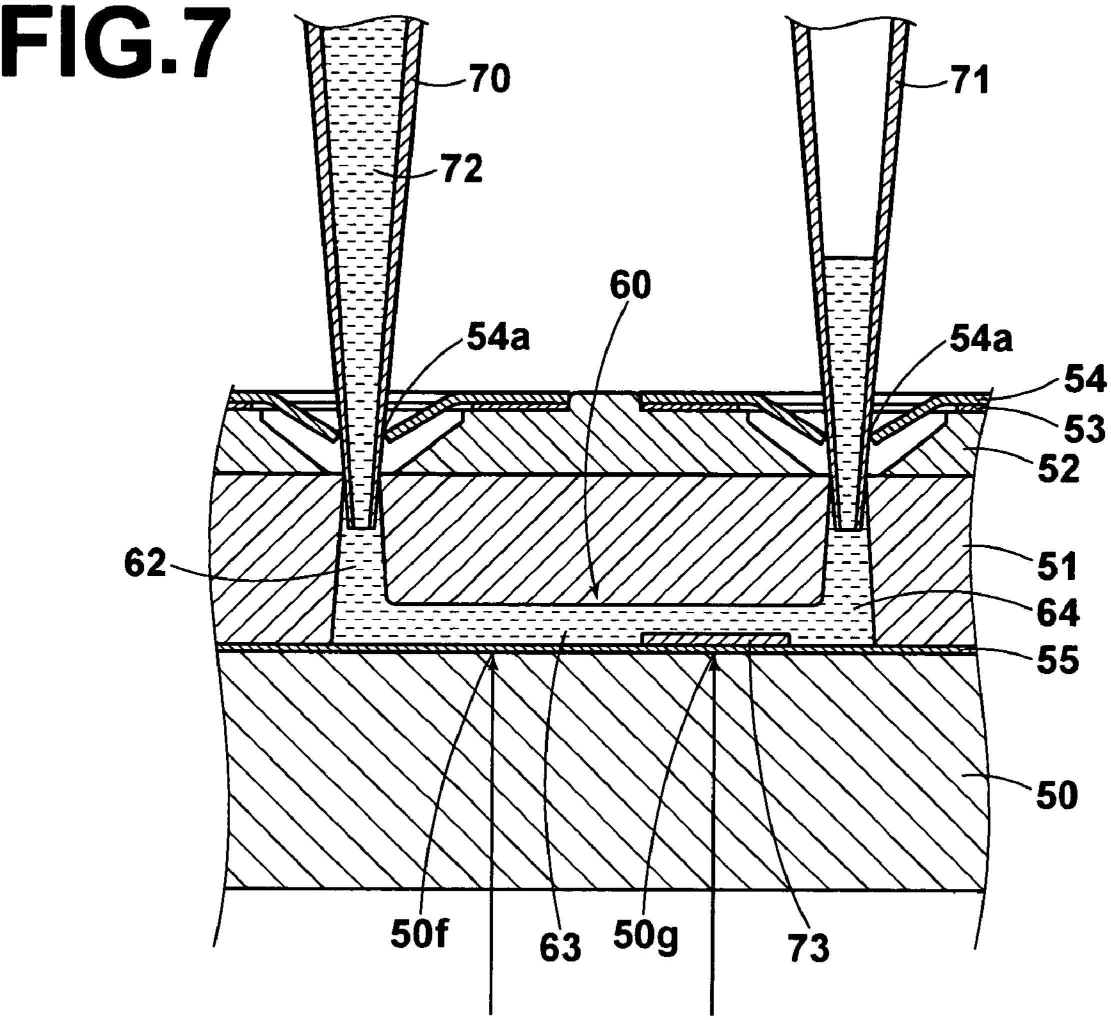
FIG. 7 is a sectional view taken along line VII-VII of FIG. 6.
Figure 8:
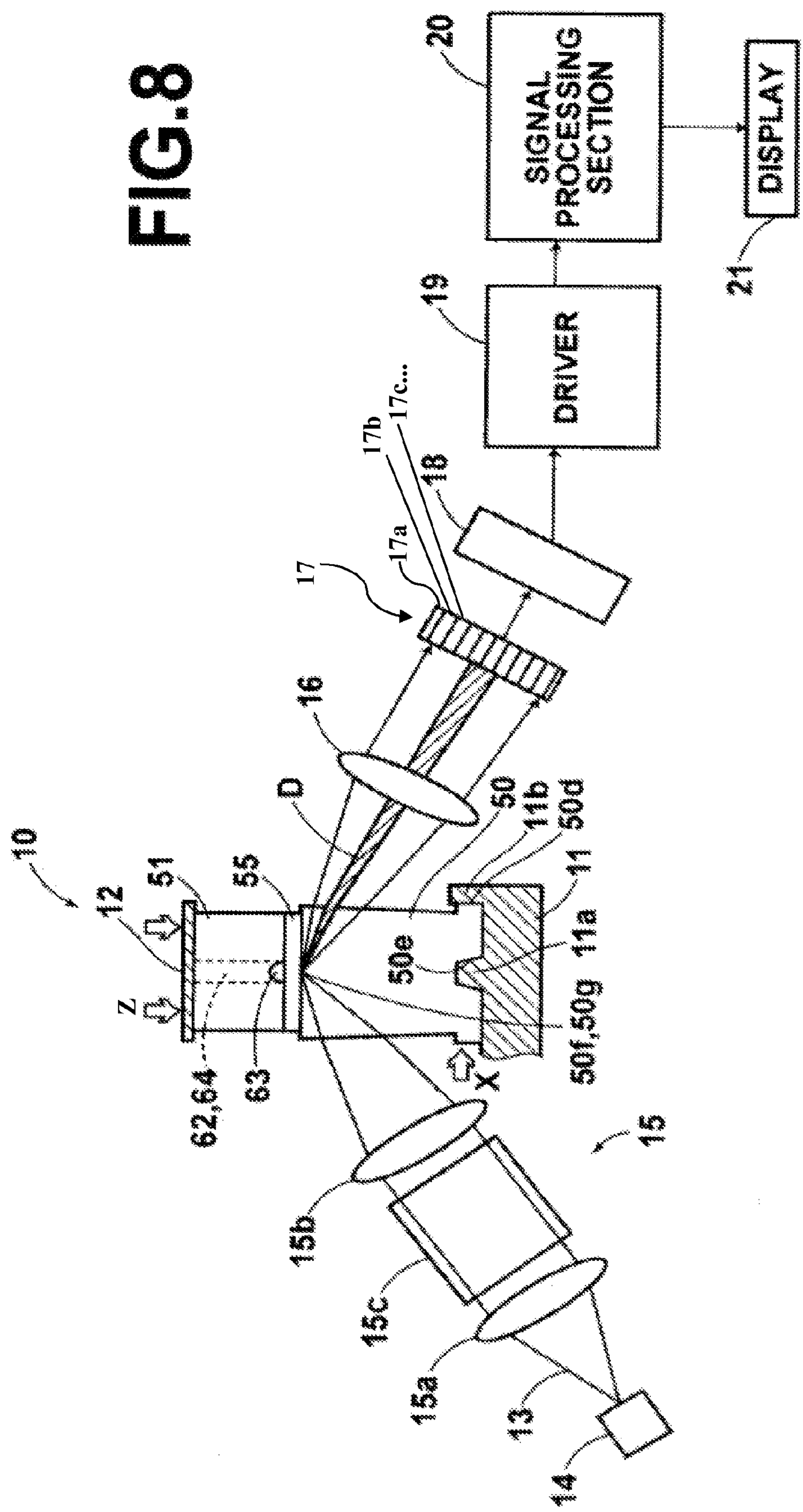
FIG. 8 is a side view of a measuring system of the surface plasmon sensor of FIG. 5.

Next, a surface plasmon sensor 1 that employs the measuring unit 10 will be described. FIG. 5 is a plan view that illustrates the schematic structure of the surface plasmon sensor 1. FIG. 6 is a plan view of a measuring system of the surface plasmon sensor 1. FIG. 7 is a sectional view taken along line VII-VII of FIG. 6. FIG. 8 is a side view of the measuring system of the surface plasmon sensor 1. Note that the holding member 52 (including the double sided tape 53 and the evaporation preventing member 54) has been omitted from FIG. 8.

As illustrated in FIG. 5, the surface plasmon sensor 1 is capable of simultaneously analyzing a plurality of samples, by causing light beams to enter the plurality of flow paths 60 of the measuring unit 10 in parallel. The surface plasmon sensor 1 is constituted by a plurality of surface plasmon measuring systems 1A, 1B, . . . In the following description of the constituent parts of each system, letters that indicate to which system the constituent parts belong (A, B, . . . ) will be omitted.

As illustrated in FIG. 6 and FIG. 8, each measuring system comprises: a light source 14 constituted by a semiconductor laser or the like (hereinafter, referred to as "laser light source 14"), for emitting a single light beam 13; an optical system 15, for separating the light beam 13 into two light beams 13 and for propagating them toward the measuring unit 10 to enter two interfaces 50*f* and 50*g* between the dielectric block 50 and the metal film 55, below the flow path 60; two collimating lenses 16 for collimating the light beams 13, which are reflected at each of the interfaces 50*f* and 50*g*; two photodiode arrays 17, for detecting each of the collimated light beams 13; a differential amplifier array 18, which is connected to the two photodiode arrays 17; a driver 19; a signal processing section 20 constituted by a computer system or the like; and a display section 21, connected to the signal processing section 20.

The incident optical system 15 comprises: a collimating lens 15*a* for collimating the light beam 13, which is emitted in a divergent state from the laser light source 14; a half mirror 15*c* for separating the collimated light beam 13 into two light beams 13; a mirror 15*d* for reflecting the light beam 13, which is reflected by the half mirror 15*c*, toward the measuring unit 10; and two condensing lenses 15*b*, each for respectively causing the light beam 13, which passes through the half mirror 15*c*, and the light beam 13, which is reflected by the mirror 15, to converge on the interface 50*f* and the interface 50*g*.

The light beams 13 are condensed as described above. Therefore, the light beams 13 include components that enter the interfaces 50*f* and 50*g* at various angles of incidence θ. Note that these angles θ are set such that they are greater than or equal to a total internal reflection angle. The light beams 13 are totally internally reflected at the interfaces 50*f* and 50*g*. The reflected light beams 13 include components, which are reflected at various reflective angles. Note that the optical system 15 may cause the light beams 13 to enter the interfaces 50*f* and 50*g* in a defocused state. If this configuration is adopted, errors in detection of states of surface plasmon resonance are averaged out, thereby improving the measurement accuracy.

Note that the light beams 13 are caused to enter the interfaces 50*f* and 50*g* as p-polarized light. To cause the light beam 13 emitted from the laser light source 14 to be p-polarized, the laser light source 14 may be arranged such that the polarization direction thereof is a predetermined direction, in advance. Alternatively, the polarization direction of the light beam 13 may be controlled by a wavelength plate.

As illustrated in FIG. 7, the light beams 13 are caused to enter the two interfaces 50*f* and 50*g*, which are within the measuring path 63 of each of the flow paths 60, in a parallel state. In the present embodiment, nothing is fixed on the metal film 55 above the interface 50*f*, while a sensing substance 73 is fixed on the metal film 55 above the interface 50*g*.

During measurement, the differential values output by the differential amplifier array 18 of the measuring system are continuously measured with the passage of time. Thereby, changes in the refractive index of the liquid sample, which is in contact with the metal film 55, and changes in the refractive index of the sensing substance 73 can be observed.

Particularly in the present embodiment, the refractive index of the sensing substance 73 changes due to bonding between the sensing substance 73 and a test target, if the test target is a specific substance that bonds with the sensing substance 73. Therefore, by measuring the aforementioned differential values, whether the test target is the specific substance that bonds with the sensing substance 73 can be detected.

Also, in the present embodiment, the metal film 55 is provided with a region on which the sensing substance 73 is not fixed, as well as the region on which the sensing substance 73 is fixed. Thereby, a reference measurement and measurement of the bonding state between the sensing substance 73 and the test target are enabled to be performed simultaneously. Therefore, measurement results, in which errors caused by temperature change of the liquid sample and the like are cancelled out, can be obtained by deriving the difference between measured values of the two regions.

Note that the present embodiment is not limited to being utilized such that the reference measurement and the measurement of the bonding state between the sensing substance 73 and the test target are simultaneously performed. Other manners of utilization, such as performing the reference measurement by employing a measurement surface of a different flow path 60, or not performing reference measurement, are also possible.

[Positioning of the Measuring Unit]

Figure 9:
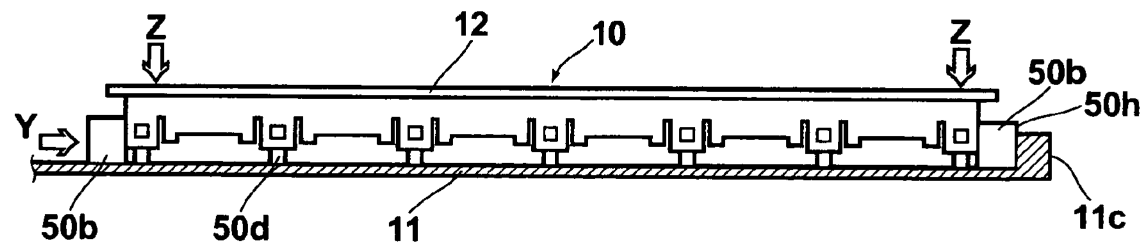
FIG. 9 is a front view that illustrates positioning directions of the measuring unit in the measuring system of the surface plasmon sensor.
Figure 16:
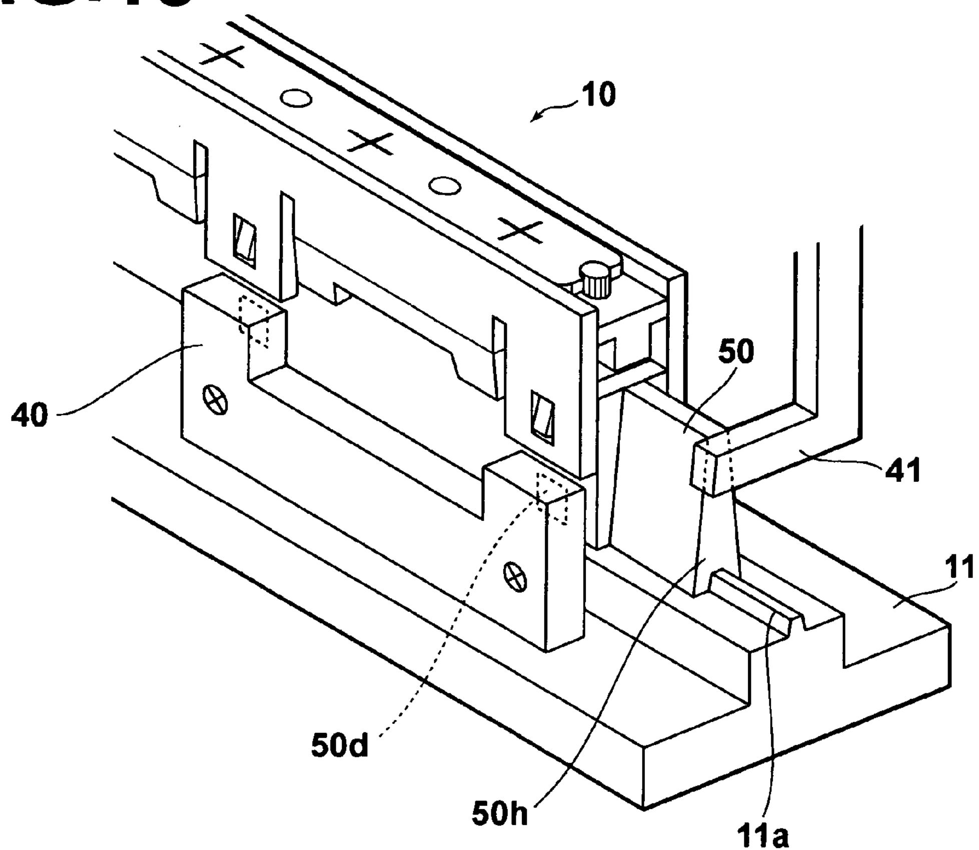
FIG. 16 is a partial magnified perspective view of a measuring unit positioning mechanism.
Figure 17:
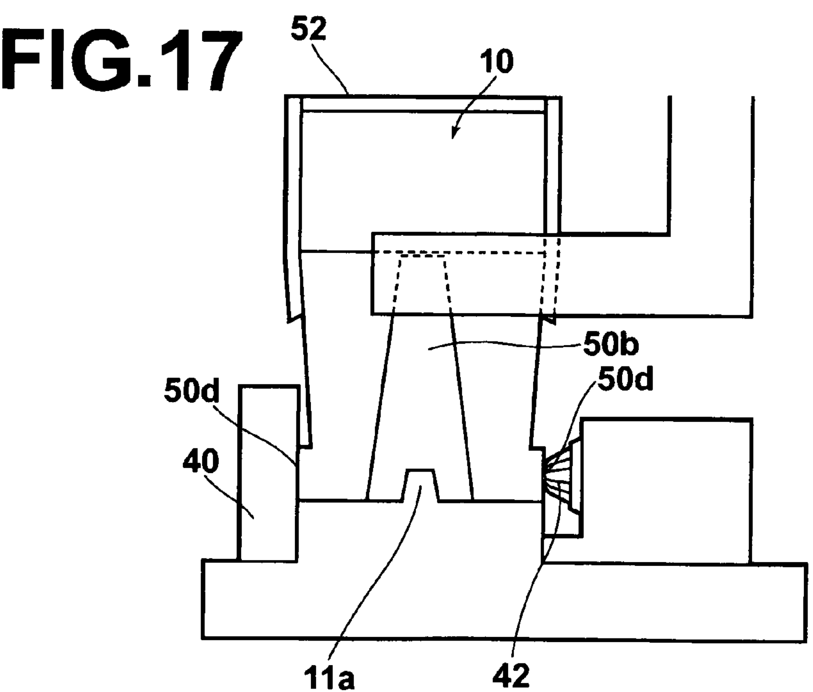
FIG. 17 is a partial magnified side view of a measuring unit positioning mechanism.

Hereinafter, positioning of the measuring unit 10 with respect to the surface plasmon sensor 1 will be described. Prior to measurement, the measuring unit 10 is conveyed from a constant temperature chamber 2 to a measurement position on a chip holding section 11 (the conveyance mechanism will be described later). A rail 11*a*, for engaging the guide groove 50*e* formed in the dielectric block 50, is formed at the chip holding section 11, enabling high positional accuracy to be secured during conveyance of the measuring unit 10. Further, after the measuring unit 10 is placed on the chip holding section 11, the dielectric block 50 is pressed by an urging mechanism (not shown) in the direction indicated by arrow X in FIG. 8. The urging mechanism presses the dielectric block 50 so that the vertical protrusions 50*d* thereof abut a stopper 11*b*, which is provided at the right side (in FIG. 8) of the chip holding section 11, thereby accurately positioning the measuring unit in the X direction. To enable accurate positioning in the X direction, there is a slight amount of play in the positioning performed by engagement of the rail 11*a* and the guide groove 50*e*. A pressing member 12, which is formed as a plate or a frame, is placed on the upper surface of the flow path forming member 51, and pressure is applied in the Z direction, to accurately position the measuring unit 10 on the chip holding section 11 in the Z direction. Further, as illustrated in FIG. 9, a stopper 11*c* is provided at the leading end (the right side end in FIG. 9) of the chip holding section 11. The end surface of the left (in FIG. 9) holding portion 50*b* is pressed such that the abutment surface 50*h* at the leading end of the right holding portion 50*b* of the dielectric block 50 abuts the stopper 11*c*. Thereby, the measuring unit 10 is positioned in the Y direction. Note that stoppers 11*b* for abutting the vertical protrusions 50*d* of the dielectric block 50 are not illustrated (alternate examples are illustrated in FIG. 16 and FIG. 17).

[Sample Analysis by the Surface Plasmon Sensor]

After the measuring unit 10 is positioned at the chip holding section 11, a liquid sample supply pipette chip 70 is inserted into the entrance 61 of the flow path forming member 51, as illustrated in FIG. 7. A liquid sample suctioning pipette chip 71 is inserted into the exit 65, and measurement is commenced after a liquid sample 72 is supplied to from the liquid sample supply pipette chip 70 the measurement path 63 of the flow path 60.

As illustrated in FIG. 8, the light beam 13 emitted from the laser light source 14 in a divergent state converges on the interface 50*f* and the interface 50*g* between the dielectric block 50 and the metal film 55, by the operation of the optical system 15. At this time, the light beams 13 include components that enter the interfaces 50*f* and 50*g* at various angles of incidence θ. Note that these angles θ are set such that they are greater than or equal to a total internal reflection angle. The light beams 13 are totally internally reflected at the interfaces 50*f* and 50*g*. The reflected light beams 13 include components, which are reflected at various reflective angles.

After being totally internally reflected at the interfaces 50*f* and 50*g*, the two light beams 13 are collimated by the two collimating lenses 16. The collimated light beams 13 are respectively detected by the two photodiode arrays 17. Each of the photodiode arrays 17 of the present embodiment are constituted by a plurality of photodiodes 17*a*, 17*b*, 17*c* . . . , which are arranged in a single row. The photodiode arrays 17 are provided such that the directions that the photodiodes 17*a*, 17*b*, 17*c* . . . are arranged are perpendicular to the direction in which the collimated light beams 13 propagate. Accordingly, each component of the light beams 13, which are reflected at various reflective angles at the interfaces 50*f* and 50*g*, is received by a different photodiode 17*a*, 17*b*, 17*c*, . . . .

In the present embodiment, the metal film 55 is provided with a region on which the sensing substance 73 is not fixed, as well as the region on which the sensing substance 73 is fixed. A reference measurement and measurement of the bonding state between the sensing substance 73 and the test target are performed simultaneously. Therefore, measurement results, in which errors caused by temperature change of the liquid sample and the like are cancelled out, can be obtained by deriving the difference between measured values of the two regions.

Note that here, the metal film 55 is the example of a reference measurement surface. It is preferable that the reference measurement surface to be that which does not bond with the test target within the liquid sample 72. Such a reference measurement surface may be formed by fixing alkyl thiol, amino alcohol, amino ether or the like onto the reference measurement surface. An antibody may be fixed to a test target measurement surface.

Note that as previously mentioned, the present embodiment is not limited to being utilized such that the reference measurement and the measurement of the bonding state between the sensing substance 73 and the test target are simultaneously performed. Other manners of utilization, such as performing the reference measurement by employing a measurement surface of a different flow path 60, or not performing reference measurement, are also possible.

The measuring apparatus is not limited to that which performs simultaneous measurements with regard to all flow paths of a measuring unit, by employing a plurality of surface plasmon measuring systems. The measuring apparatus may comprise a single surface plasmon measuring system, and may perform measurements regarding each of the flow paths of a measuring unit sequentially, by moving the position of the measuring unit relative to the measuring system.

[Entire Construction of the Surface Plasmon Sensor]

Hereinafter, the basic structure of a surface plasmon sensor that utilizes the one dimensional measuring unit 10 of the present invention to analyze samples, including the conveyance mechanism for the measuring unit 10, will be described. In addition, an example of the conveyance mechanism for the measuring unit 10 will be described.

Figure 10:
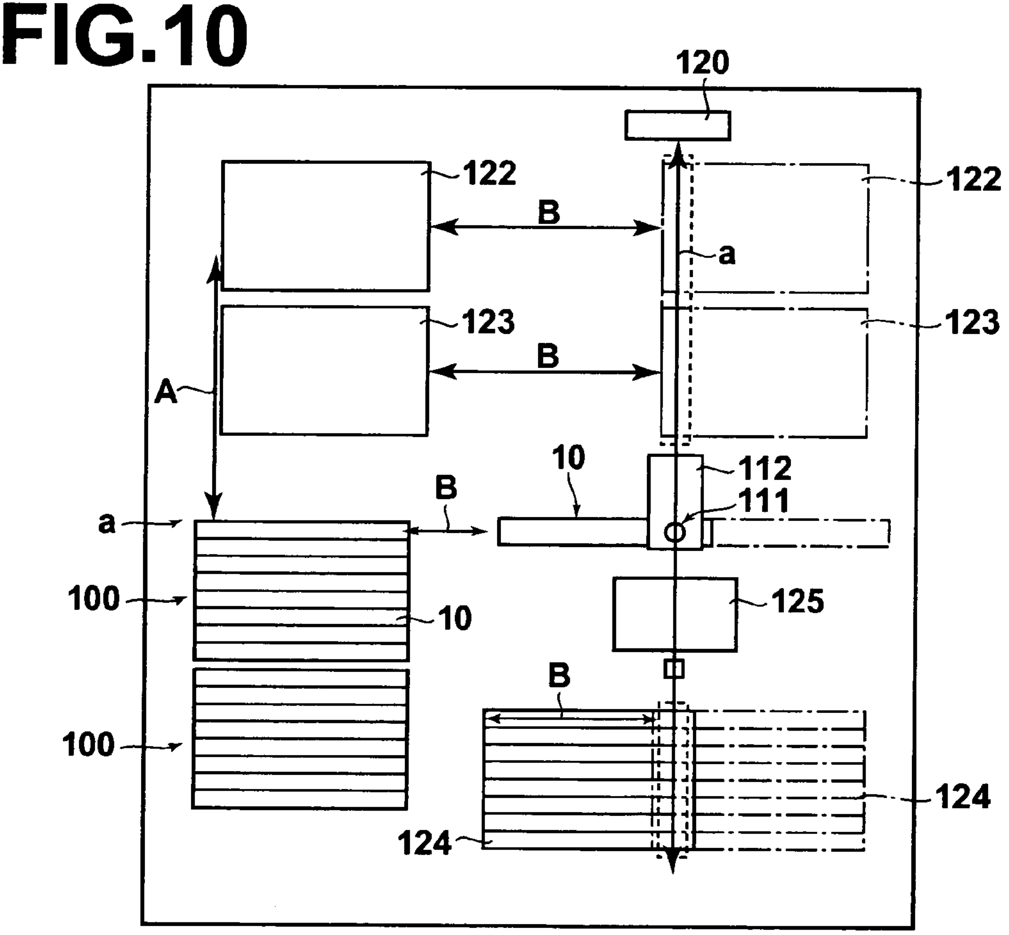
FIG. 10 is a plan view that illustrates the entire schematic construction of a surface plasmon sensor.
Figure 11:
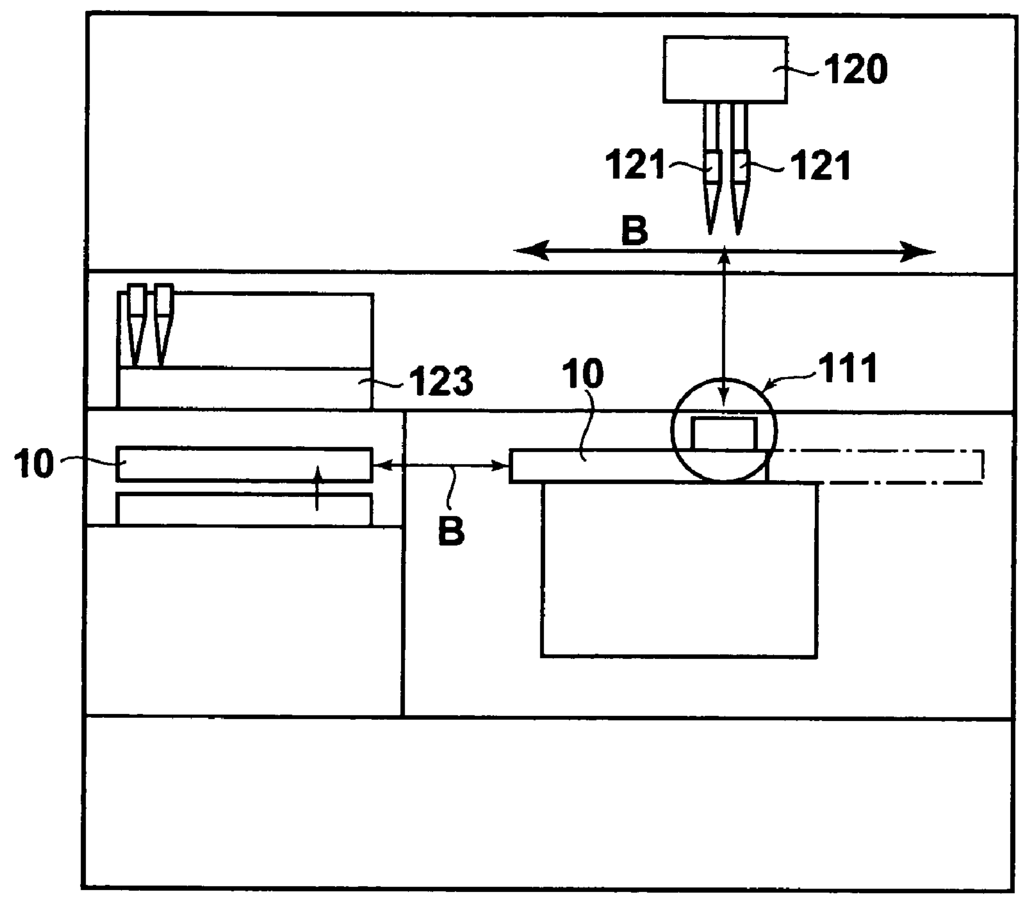
FIG. 11 is a front view of the surface plasmon sensor of FIG. 10.
Figure 12:
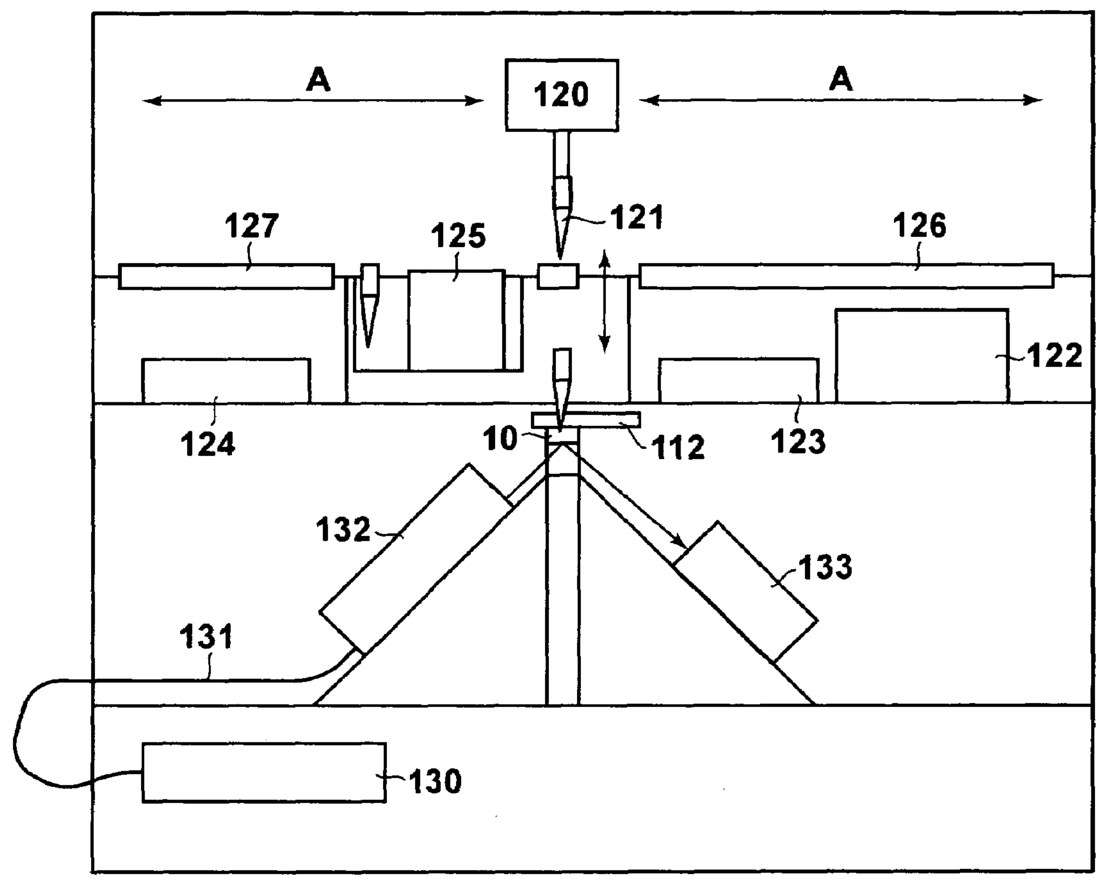
FIG. 12 is a side view of the surface plasmon sensor of FIG. 10.
Figure 13:
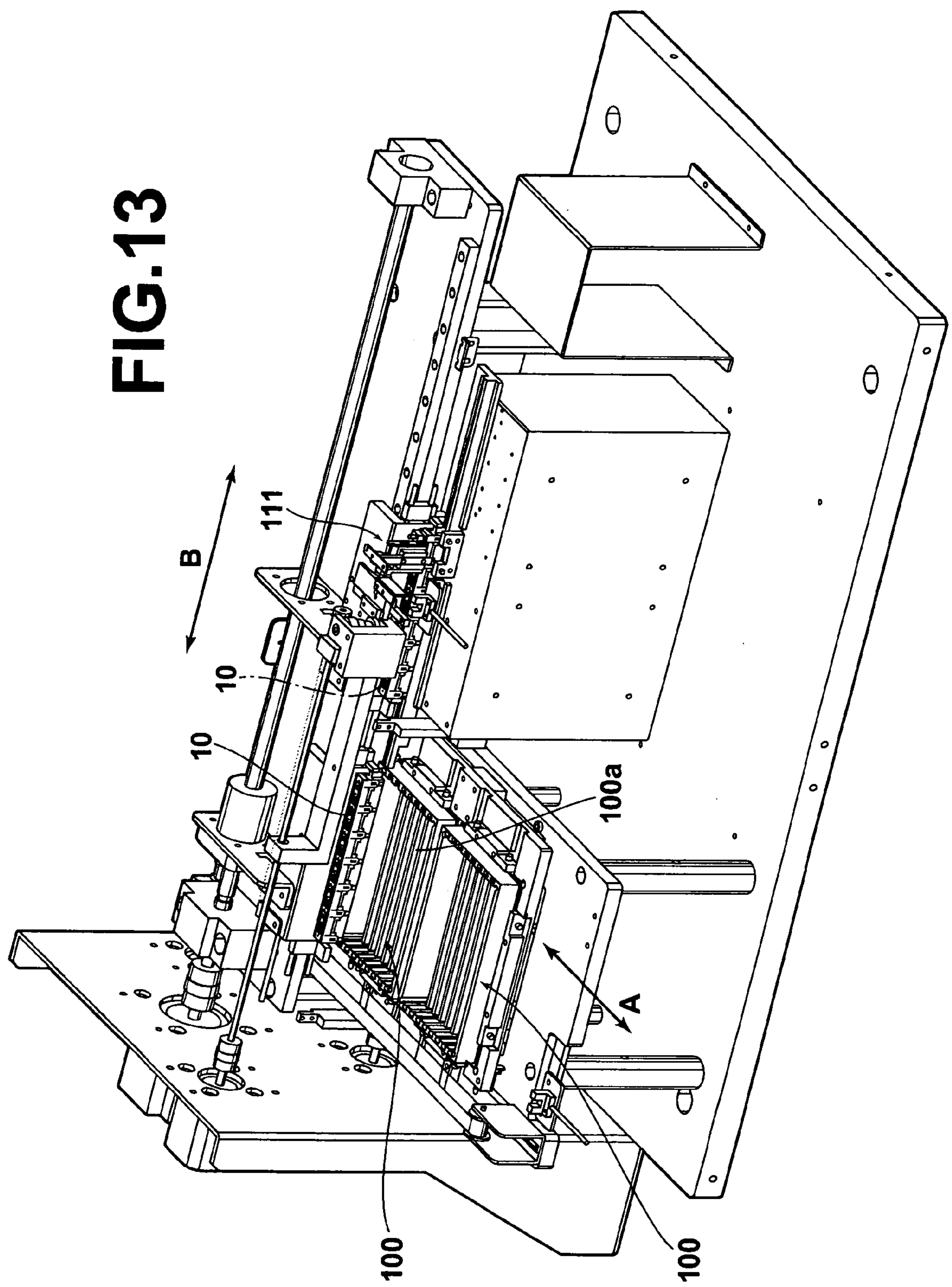
FIG. 13 is a perspective view illustrating a conveyance mechanism for the measuring unit.
Figure 14:
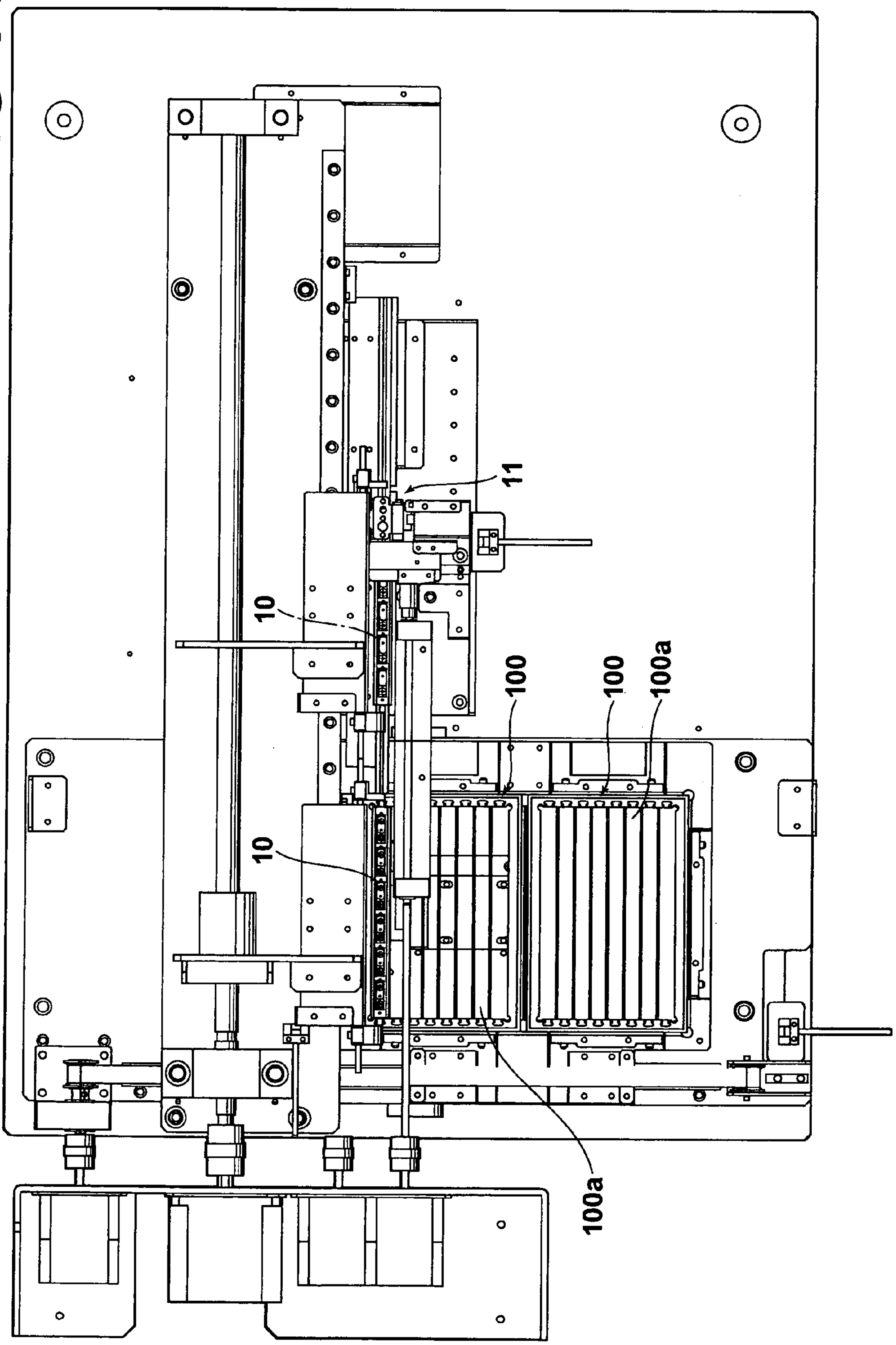
FIG. 14 is a plan view of the conveyance mechanism of FIG. 13.
Figure 15:
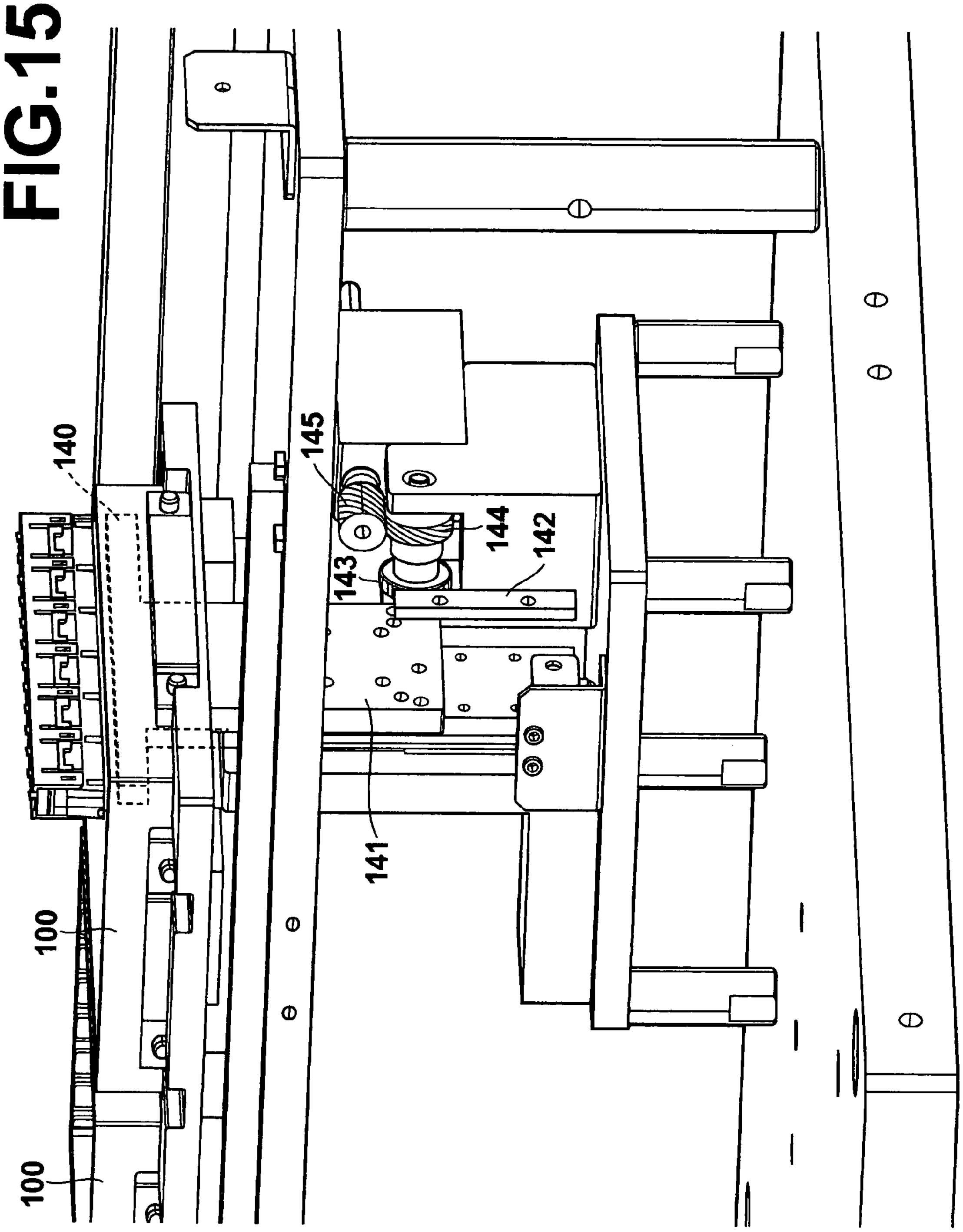
FIG. 15 is a partial front view of a measuring unit thrusting mechanism of the conveyance mechanism.

FIG. 10 is a plan view that illustrates the entire schematic construction of a surface plasmon sensor. FIG. 11 is a front view of the surface plasmon sensor of FIG. 10. FIG. 12 is a side view of the surface plasmon sensor of FIG. 10. FIG. 13 is a perspective view illustrating the conveyance mechanism for the measuring unit 10. FIG. 14 is a plan view of the conveyance mechanism of FIG. 13. FIG. 15 is a partial front view of a measuring unit thrusting mechanism of the conveyance mechanism.

In the surface plasmon sensor of the present embodiment, two unit plates 100 that house eight one dimensional measuring units 10 (hereinafter, referred to as "unit 10") are arranged next to each other. This configuration enables simultaneous measurement of sixteen units 10. The unit plates 100 are capable of moving over a distance equal to the width of sixteen units 10 in a direction A, which is perpendicular to the longitudinal direction of the units 10. All sixteen of the units 10 are moved in a direction B, which is perpendicular to the direction A, at a unit thrusting position a, such that all of the measurement paths 60 of the units 10 can move through a measuring station 111. A well press 112, which is different from the pressing member 12 that presses the unit 10 across the entire length thereof, is provided at the measuring section 111. The well press 112 only presses the portion of the unit 10, which is positioned at the measuring section 111, in the Z direction, thereby positioning the measurement path 63 to be measured.

A dispensing head 120, equipped with chips 121 for supplying and discharging (suctioning) liquids, is enabled to enter and exit the measuring section 111. The dispensing head 120 is capable of moving from the very top to the very bottom of FIG. 10, along direction A. A chip supply section 122, at which a great number of the chips 121 are arranged in a matrix, is provided in the surface plasmon sensor at the very top of FIG. 10. The chip supply section 122 is configured to move along direction B, such that all of the chips 121 are enabled to be picked up by the dispensing head 120, which moves along direction A. A titer plate 123, in which a great number of analytes employed in measurements are arranged in a matrix, is provided such that it is capable of moving along direction B. The titer plate is configured to move along direction B up to the trajectory of movement of the dispensing head 120 along direction A, such that all of the analytes are enabled to be suctioned by the chip 121 of the dispensing head 120. A 386 titer plate, in which dispensing can be performed at 96 locations at every other spot in both the rows and columns thereof, may be utilized as the titer plate 123.

Further, a 96 well plate 124 is provided at the lower portion of FIG. 10. The 96 well plate 124 houses DMSO solution at different concentrations, such as: low concentration; medium low concentration; medium concentration; medium high concentration; and high concentration. The 96 well plate 124 is also capable of movement along direction B, such that the chip 121 of the dispensing head 120 is enabled to suction all of the samples and all of the buffer solutions.

A liquid disposal section 125 is provided between the 96 well plate 124 and the measuring section 111. The liquid disposal section 125 suctions liquid, which is discharged from the unit and is to be disposed, from the pipette chips and disposes of them. The dispensing head 120 expels liquid at the liquid disposal section 125.

Measurement is performed in the following order. First, a unit, in which a sensing substance is provided on a portion of the metal film 55 in advance, is moved from the unit plate 100 to the measuring section 111, along direction B. The measurement path 63 to be measured is positioned and fixed at the measuring section 111. Then, a fresh chip 121 is mounted on the dispensing head 120 at the chip supply section 122. The dispensing head 120 moves along direction A to the 96 well plate, suctions the low concentration DMSO solution, and supplies the low concentration DMSO solution to the measurement path 63 of the unit 10. Measurement is performed, then the DMSO solution is discharged. In a similar manner, suction, supply, measurement, and discharge using the medium concentration and the high concentration DMSO solutions are performed. In this manner, measurements are performed for the different concentrations of DMSO solution, to enable DMSO correction. Next, the dispensing head 120 moves to the titer plate 123, suctions an analyte, moves along direction A, then supplies the analyte to the unit 10. A reaction is waited for, measurement is performed, and then the analyte is discharged. Thereafter, the dispensing head 120 moves to the 96 well plate 124, suctions a buffer solution, and supplies the buffer solution to the unit 10. Measurement is performed, then the buffer solution is discharged. The chip 121 is cleansed with the buffer solution, and then discarded. The refractive index of the analyte is derived, based on data regarding the DMSO concentrations obtained by the operations described above.

By the above operations, measurement of a single measurement path 63, on which the sensing substance is fixed, is completed regarding a single analyte. Next, the unit 10 is moved along direction B to position the next measurement path 63 at the measuring section 111, and the above operations are repeated to perform measurement regarding a different analyte.

Note that as illustrated in FIG. 11, the chips 121 are provided in pairs. This configuration enables the pair of chips 121 to enter the entrance 61 and the exit 65 of the unit simultaneously. Thereby, liquid can be supplied from the entrance 61 and discharged from the exit 65 simultaneously.

The regions above the chip supply section 122, the titer plate 123, and the 96 well plate 124 are an analyte/chip opening 126 and a sample opening 127. The chips 121 move vertically through the analyte/chip opening 126 and the sample openint 127, to access the chip supply section 122, the titer plate 123, and the 96 well plate.

A laser light source 130; an optical system 132 including a beam splitter, a shutter and the like, for causing laser light to enter the unit 10; an optical fiber 131 that connects the laser light source 130 and the optical system 132; and a light receiving section 133, for receiving the light reflected at the metal film 55 of the unit 10, are provided below the measuring section.

[Conveyance of the Measuring Units]

The mechanism for conveying the units 10 is illustrated in FIG. 13, FIG. 14, and FIG. 15. The two unit plates 100 that house eight one dimensional measuring units 10 (although they are empty in the figures) are capable of movement along direction A. The thrusting mechanism thrusts the units 10 upward, and the units 10, which are thrust upward, are moved along direction B, and the measurement path 63 to be measured is positioned at the measuring section 111. As illustrated in FIG. 15, the thrusting mechanism comprises a thrusting plate 140 that thrusts the units 10 upward from below. The thrusting plate 140 is provided such that it thrusts the units 10 upward through slits 100*a* (refer to FIG. 13 and FIG. 14), which is formed in the bottom of the unit plate 100. The lower portion 141 of the thrusting plate 140 is integrally formed with a rack 142, to which a pinion 143 is engaged. A worm wheel 144, which is coaxial with the pinion 143, is rotated by a worm gear 145, and the thrusting plate 140 is configured to move vertically by forward and reverse rotations of the worm gear 145.

The positioning mechanism of the apparatus of the present embodiment is illustrated in FIG. 16 and FIG. 17. A side surface stopper 40 abuts the vertical protrusions 50*d* of a side surface of the unit 10. A leading end stopper 41 abuts the leading end surface 50*h* of the holding portion 50*b*. As illustrated in FIG. 17, a side surface pressing section 42 is provided at the side of the unit 10 opposite the side at which the side surface stopper 40 is provided. The side surface pressing section 42 abuts and presses the vertical protrusions 50*d* at a position where the measuring path 63 reaches the measuring section 111, to press the dielectric block 50 against the side surface stopper 40, thereby accurately positioning the unit 10.

The positioning mechanism of the apparatus described above enables accurate positioning of the unit 10. In addition, the unit 10 is fixed with a great amount of force. Therefore, an advantageous effect is obtained, in that the unit 10 does not move during insertion and extraction of the chips 121.

What is claimed is:

1. A one dimensional measuring unit, comprising:

an elongate dielectric block, which is transparent with respect to a light beam;

a thin film layer, formed on a flat surface of the dielectric block; and a flow path forming member, which is in close contact with the thin film layer of the dielectric block, for forming a plurality of flow paths in the longitudinal direction of the dielectric block on the thin film layer, with intervals therebetween;

each of the plurality of flow paths being constituted by: a measurement path, formed on the thin film layer; a supply path that extends from the entrance of the flow path forming member to the measurement path; and a discharge path that extends from the measurement path to the exit of the flow path forming member;

a linear guide groove for conveyance being formed in the bottom surface of the dielectric block in the longitudinal direction thereof; and positioning abutment surfaces being formed on the side surfaces and a first end surface of the dielectric block.

2. A one dimensional measuring unit as defined in claim 1, wherein:

the positioning abutment surfaces of the side surfaces and the first end surface are formed on the side surfaces in the vicinity of the bottom surface and on the first end surface in the vicinity of the bottom surface.

3. A one dimensional measuring unit as defined in claim 1, wherein:

the dielectric block comprises a main body having a trapezoidal shape, in which the bottom edge is shorter than the upper edge in a cross section perpendicular to the longitudinal direction thereof; and a holding portion, which is of a thinner width than that of the main body, is formed at each end of the main body in the longitudinal direction thereof.

4. A one dimensional measuring unit as defined in claim 2, wherein:

the dielectric block comprises a main body having a trapezoidal shape, in which the bottom edge is shorter than the upper edge in a cross section perpendicular to the longitudinal direction thereof; and a holding portion, which is of a thinner width than that of the main body when viewed from above, is formed at each end of the main body in the longitudinal direction thereof.

5. A one dimensional measuring unit as defined in claim 3, further comprising:

a holding member, for engaging with the dielectric block and for holding the flow path forming member at the upper surface of the dielectric block.

6. A one dimensional measuring unit as defined in claim 5, wherein:

the holding member comprises extension portions that extend in the longitudinal direction of the main body of the dielectric block, along the side surfaces thereof;

engaging apertures are formed in the extension portions; and engaging protrusions, for engaging the engaging apertures, are formed on the side surfaces of the main body of the dielectric block.

7. A one dimensional measuring unit as defined in claim 6, wherein:

vertically extending protrusions are formed on both side surfaces of the dielectric block in the vicinity of the bottom surface thereof, such that each pair of the vertically extending protrusions face each other, and such that the surfaces of the vertically extending protrusions formed on each of the side surfaces are parallel to each other.

8. A one dimensional measuring unit as defined in claim 1, further comprising:

a holding member, for engaging with the dielectric block and for holding the flow path forming member at the upper surface of the dielectric block.

9. A one dimensional measuring unit as defined in claim 1, wherein:

exits of the supply paths and entrances of the discharge paths are open at the lower portion of the flow path forming member; and seals that surround the exits of the supply paths and the entrances of the discharge paths are formed at the region of the bottom surface of the flow path forming member that contacts the surface of the thin film layer.

* * * * *